(12) United States Patent
Kim et al.

(10) Patent No.: US 8,940,783 B2
(45) Date of Patent: Jan. 27, 2015

(54) PHEOPHORBIDE-α CONJUGATES AND THEIR USES

(75) Inventors: Yong-Chul Kim, Gwangju (KR); Hyo Jin Ko, Gwangju (KR); Hyun You, Chungcheongbuk-do (KR); Jung-Hoon Yoon, Daejeon (KR); Hyo-Eun Yoon, Daejeon (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 13/563,974

(22) Filed: Aug. 1, 2012

(65) Prior Publication Data

US 2013/0210756 A1 Aug. 15, 2013

(30) Foreign Application Priority Data

Jan. 30, 2012 (KR) .................. 10-2012-0008901

(51) Int. Cl.
*A61K 41/00* (2006.01)
*A61K 47/48* (2006.01)

(52) U.S. Cl.
CPC ......... *A61K 41/0076* (2013.01); *A61K 41/0071* (2013.01); *A61K 47/481* (2013.01)
USPC ........................................ 514/410; 540/145

(58) Field of Classification Search
USPC ....................................................... 540/145
See application file for complete search history.

(56) References Cited

PUBLICATIONS

You, Hyun et al.; "Synthesis of Pheophorbide-alpha Conjugates with Anticancer Drugs as Potential Cancer Diagnostic and Therapeutic Agents" Bioorganic & Medicinal Chemistry, 2011, pp. 5383-5391, vol. 19.

Verma, Sarika et al.; "Strategies for Enhanced Photodynamic Therapy Effects; Photochemistry and Photobiology", 2007, pp. 996-1005, vol. 83.

Gacio, Ana Fernandez et al.; "Photodynamic Cell-Kill Analysis of Breast Tumor Cells With a Tamoxifen-Pyropheophorbide Conjugate" Journal of Celluar Biochemistry; 2006, pp. 665-670, vol. 99.

Global Leadership for New Drug Discovery and Development "Proceedings of the Fall International Convention of The Pharmaceutical Society of Korea", Nov. 7-9, 2011 Songdo Convensia, Incheon Korea.

*Primary Examiner* — Brian McDowell
(74) *Attorney, Agent, or Firm* — Nath, Goldberg & Meyer; Tanya E. Harkins

(57) ABSTRACT

The present invention relates to a pheophorbide-α conjugate or its salt, solvate or hydrate. The pheophorbide-α conjugate of the present invention exhibiting fluorescence upon its introduction into cells and degradation inhibits the survival of various cancer cells. Especially, the conjugate of pheophorbide-α (1) and doxorubicin shows higher fluorescence intensity at lower pH (cancer environment). Therefore, the present composition for photodynamic therapy (PDT) of cancers is also very useful in detecting cancers. Interestingly, the anticancer effects of the present composition are dually exerted with help of both the photosensitizer and the anticancer drug of the present conjugates.

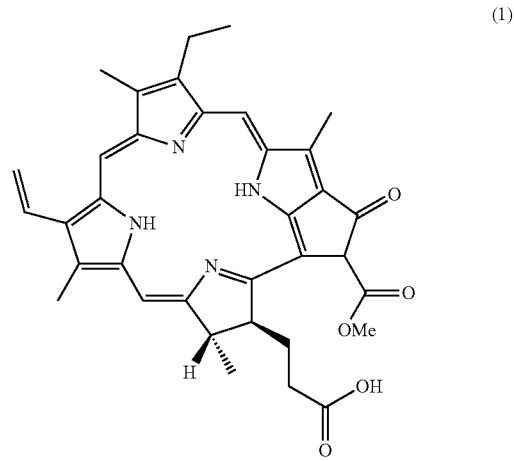

(1)

5 Claims, 8 Drawing Sheets

Pa, 1

DOX, 2

6

7

10

13

6

7

US 8,940,783 B2

PHEOPHORBIDE-α CONJUGATES AND THEIR USES

CROSS-REFERENCE TO RELATED APPLICATIONS

This application claims priority from Korean Patent Application No. 2012-0008901, filed on Jan. 30, 2012, in the Korean Intellectual Property Office, the disclosure of which is incorporated herein by reference.

BACKGROUND OF THE INVENTION

1. Field of the Invention

The present invention relates to pheophorbide-α conjugates and their uses.

2. Description of the Related Art

Many drugs are designed based on the prodrug approach as the reason for improvement of physicochemical, biopharmaceutical or pharmacokinetic properties (Jarkko, R. et al., Nat. Rev. Drug Discov. 2008, 7, 225). Chemical linker, targeting-ligand, membrane transporter, and polymer have been used as the prodrug conjugation motives (Rubi, M. et al., Adv. Drug Deliv. Rev. 2011, 63, 659). As one of the targeting-ligand, photosensitizers have been utilized in the development of cancer diagnostic agents as well as in photodynamic therapy (PDT) which could treat cancer and non malignant tumor by reactive oxygen species generated by light, oxygen and photosensitizer (Sarika, V. et al., Photochem. Photobiol. 2007, 83, 996). Several photosensitizer conjugates have been developed. The carbohydrate moieties on conjugation with 3-(10-hexyloxyethyl)-3-devinyl pyropheophorbide-α (HPPH) (Xiang, Z et al., J. Med. Chem. 2009, 52, 4306), porphyrin conjugates with monocolonal antibodies (Karen, S. et al., Immunology 2010, 132, 256) and with spermine (Frank, H. et al., Chem. Med. Chem. 2008, 3, 1185), pyropheophorbide conjugate with tamoxifen (Ana, F. G. et al., J. Cell. Biochem. 2006, 99, 665), tetra(pentafluorophenyl)porphyrin conjugate with thiosaccharide (Xin, C. et al., Biochemistry 2004, 43, 10918), and Chlorin p6 and histamine conjugate (Arpana, P. et al., Cancer Chemother. Pharmacol. 2011, 68, 359) were reported to increase cellular accumulation of photosensitizer in tumor cells. In addition, anticancer drugs such as doxorubicin have been reported that their conjugated compounds enhanced selective cellular uptake and reduced the side effects (Yoshiyuki, Y. et al., Bioorg. Med. Chem. Lett. 2008, 18, 1632; Yu-Fen, H. et al., Chem. Biol. Chem. 2009, 10, 862; Paul, A. V. et al., on behalf of the Cancer Research Campaign Phase I/II Committee Clin. Cancer Res. 1999, 5, 83; Vanangamudi, A. N. C. et al., Biomed. Mater. Res. A 2010, 94A, 730). Pheophorbide-α (Pa, 1) is a chlorine based photosensitizer derived from chlorophyll-α with photo-dependent or -independent cytotoxic activity (Ritu, B. et al., J. Mol. Struct. 1994, 327, 201; Prapai, W. et al., Bioorg. Med. Chem. 2002, 10, 583).

The present inventors reported our investigations on the effects of pheophorbide-α conjugates with anticancer drugs such as doxorubicin (DOX, 2) and paclitaxel (PTX, 3) (FIG. 1) either by direct coupling or via linkers which are known for the characteristics of selective cleavage in cancer cell. The analysis of fluorescence spectrum, cellular uptake using confocal microscopy and in vitro anti-cancer activities in various cancer cell lines of the new pheophorbide-α conjugates are reported.

Throughout this application, various patents and publications are referenced and citations are provided in parentheses. The disclosure of these patents and publications in their entireties are hereby incorporated by references into this application in order to more fully describe this invention and the state of the art to which this invention pertains.

SUMMARY OF THE INVENTION

The present inventors have made intensive researches to develop novel substance for preventing or treating cancers, that is capable of not only inhibiting cancer cell proliferation but also being used as a photosensitizer for photodynamic therapy (photodynamic therapy, PDT). As a result, we have synthesized novel conjugated compounds by combining photosensitizer pheophorbide-α and the anticancer drug, doxorubicin or paclitaxel. Then, we have elucidated that these conjugations inhibit the survival of various cancer cells and exhibit fluorescence when they are introduced into cells and degraded. Especially, it has been identified that the conjugate of pheophorbide-α and doxorubicin shows higher fluorescence intensity at lower pH (cancer environment).

Therefore, it is an object of this invention to provide a pheophorbide-α conjugate or a pharmaceutically acceptable salt, solvate, or hydrate thereof.

It is another object of this invention to provide a pharmaceutical composition for preventing or treating cancers.

It is still another object of this invention to provide a photosensitizer composition for detecting cancers.

Other objects and advantages of the present invention will become apparent from the detailed description to follow taken in conjugation with the appended claims and drawings.

DETAILED DESCRIPTION OF THIS INVENTION

Figure 1A:
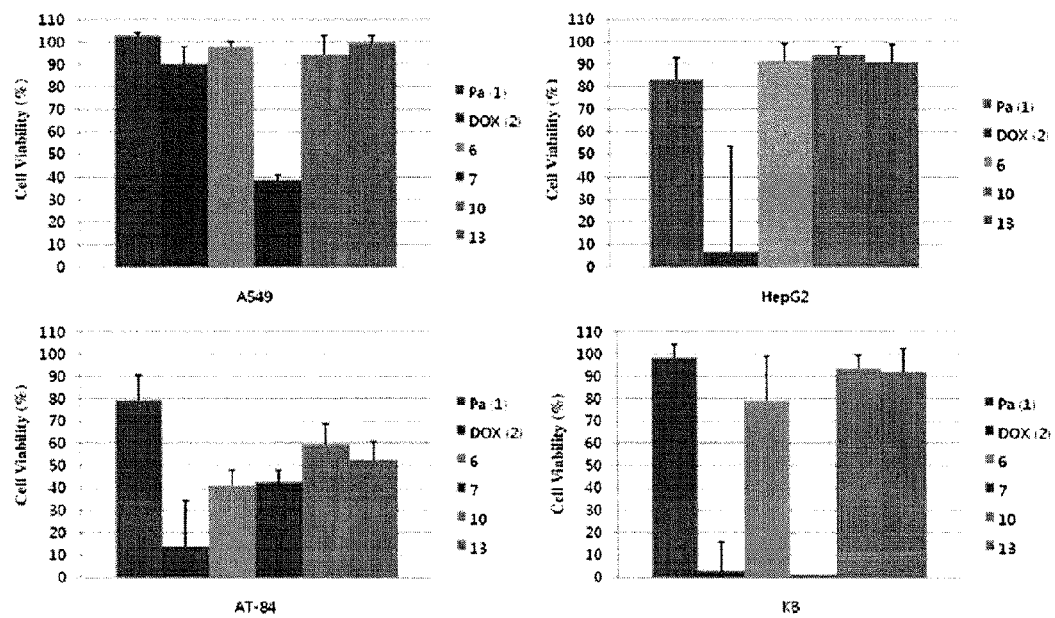
FIGS. 1a-1c show cancer cell viability after 3 days in the presence of 10 µM concentrations of Pa (1), DOX (2) and conjugates (6, 7, 10, and 13).
Figure 1B:
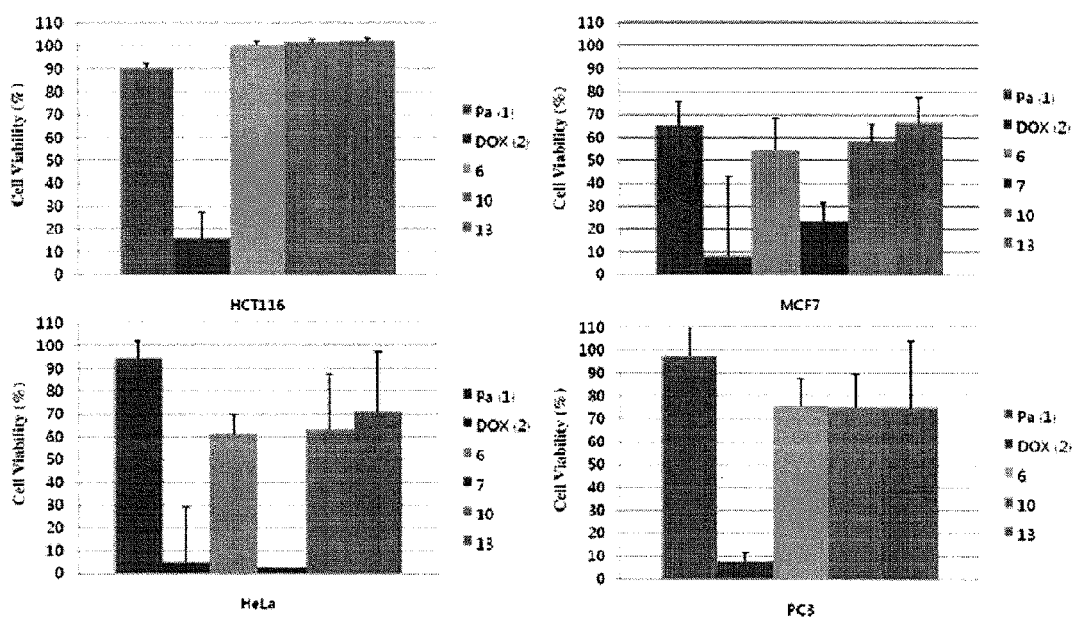
Figure 1C:
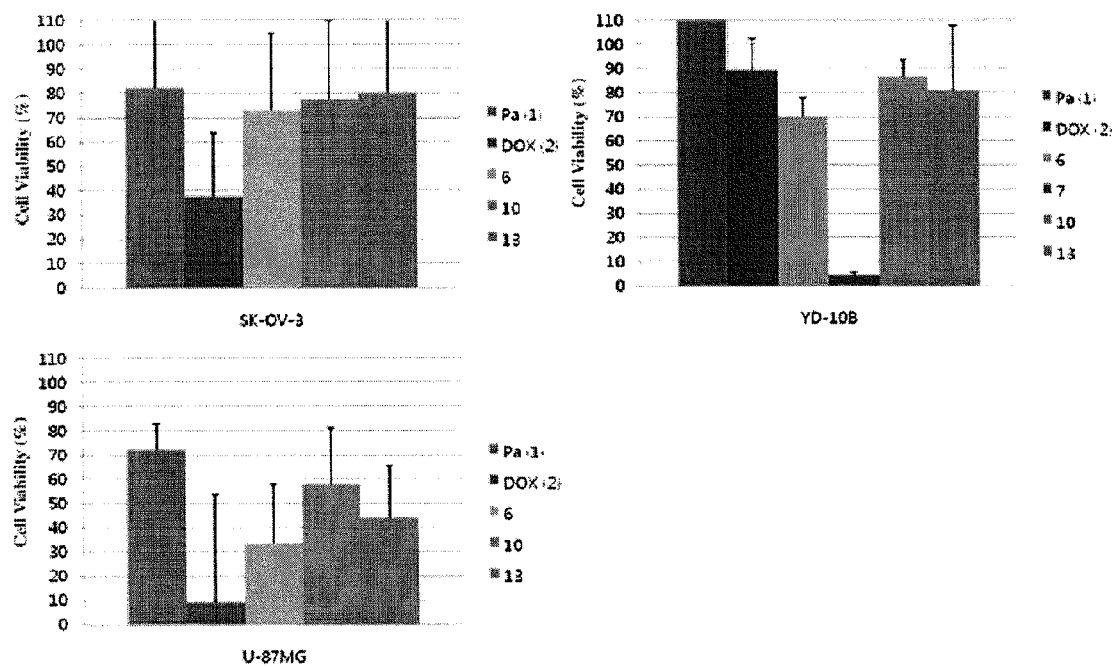
Figure 2A:
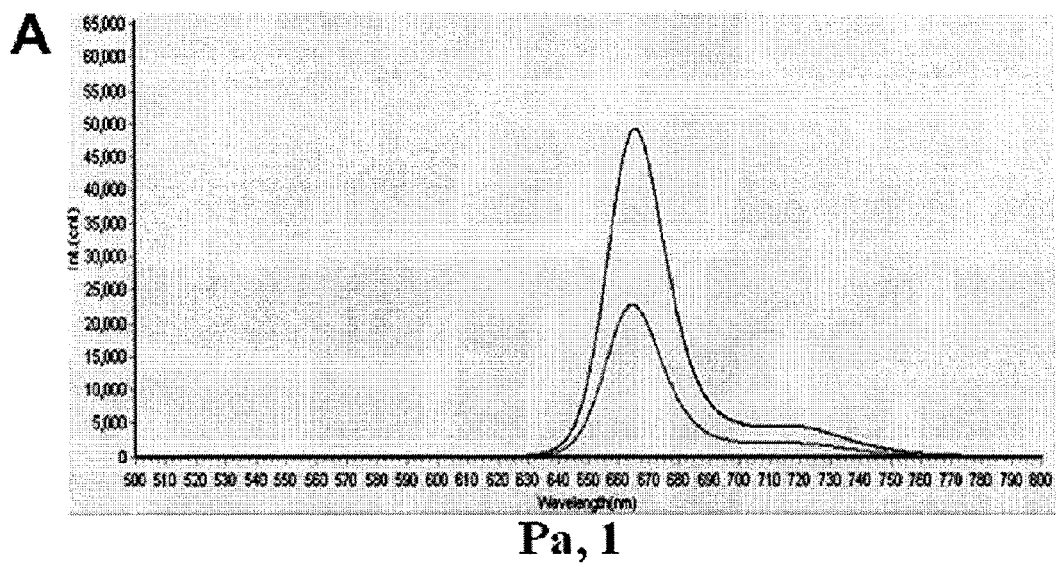
FIGS. 2a-2f represent fluorescence spectra of Pa (A), DOX (B) and conjugates (C-F). The emission wavelength with 420 and 440 nm excitation wavelength was shown in blue and red, respectively.
Figure 2B:
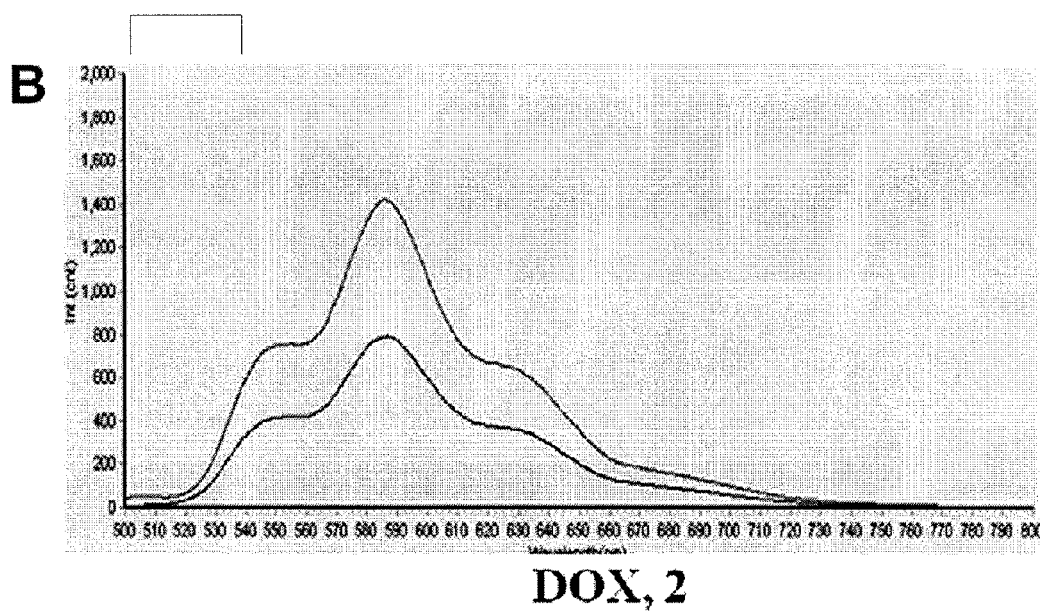
Figure 2C:
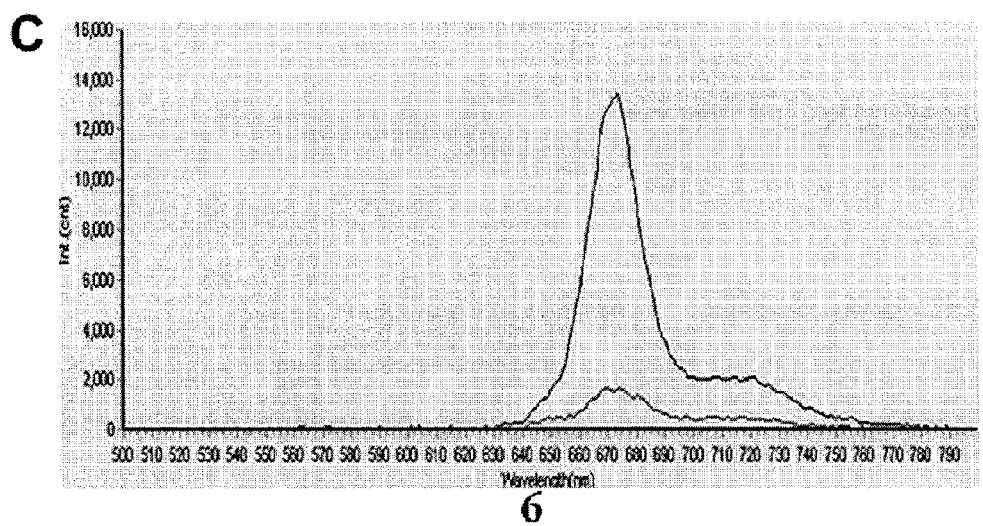
Figure 2D:
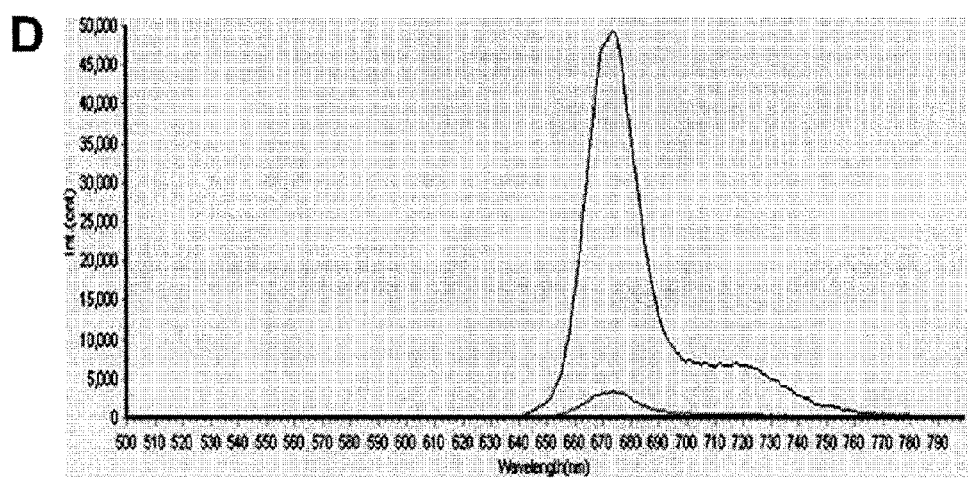
Figure 2E:
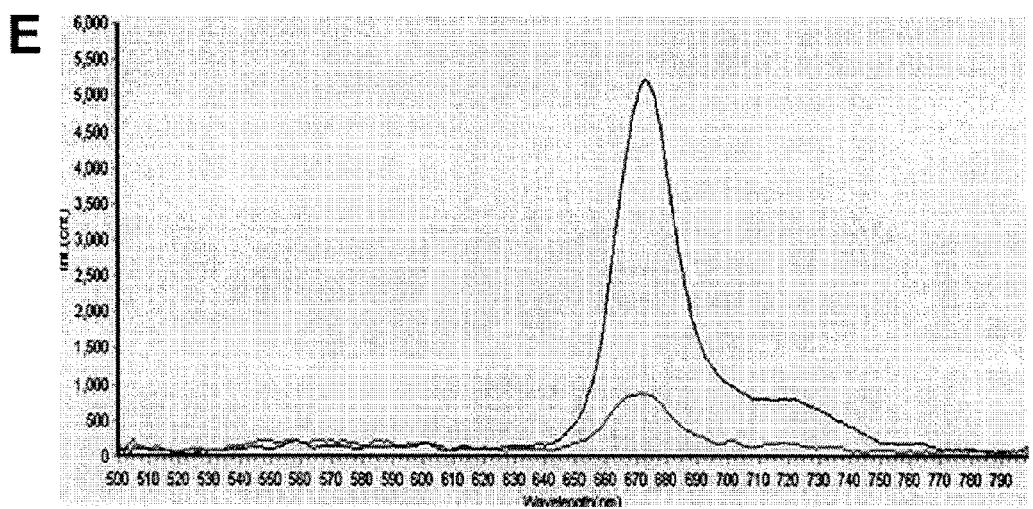
Figure 2F:
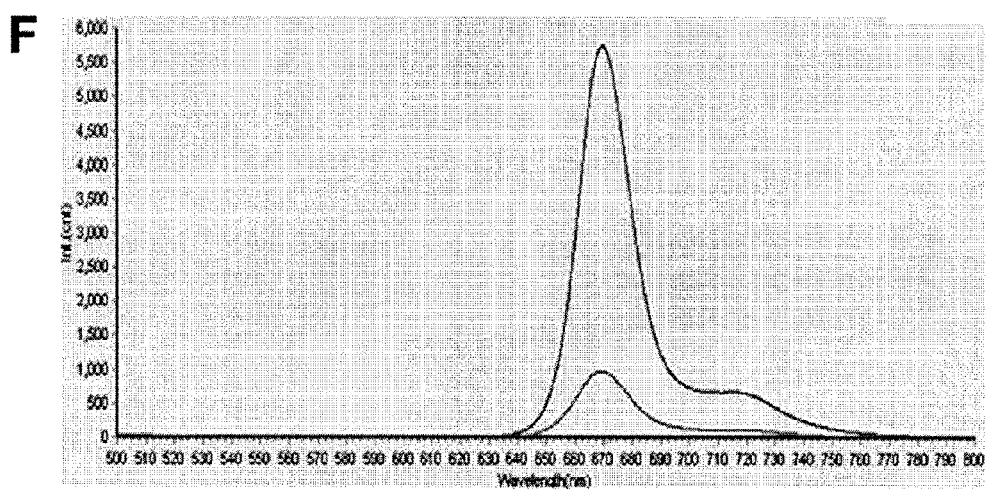

In one aspect of the present invention, there is provided a pheophorbide-α conjugate comprising (i) a first compound represented by the following Formula 1 and a second compound represented by the following Formula 2; or (ii) a first compound represented by the following Formula 1 and a second compound represented by the following Formula 3:

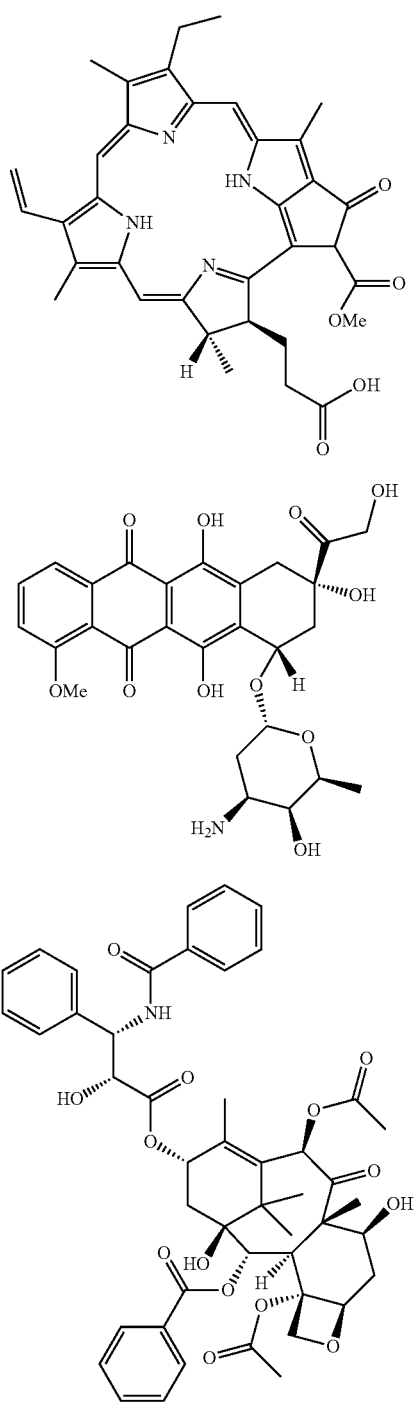

or a pharmaceutically acceptable salt, solvate, or hydrate thereof.

In another aspect of this invention, there is provided a pharmaceutical composition for preventing or treating cancers, comprising (a) a pharmaceutically effective amount of the pheophorbide-α conjugate; and (b) a pharmaceutically acceptable carrier.

In still another aspect of this invention, there is provided a photosensitizer composition for detecting cancers, comprising the pheophorbide-α.

In further aspect of this invention, there is provided a method for preventing or treating cancers, comprising administering to a subject a pharmaceutical composition comprising (a) a pharmaceutically effective amount of the pheophorbide-α conjugate; and (b) a pharmaceutically acceptable carrier.

The present inventors have made intensive researches to develop novel substance for preventing or treating cancers, that is capable of not only inhibiting cancer cell proliferation but also being used as a photosensitizer for photodynamic therapy (photodynamic therapy, PDT). As a result, we have synthesized novel conjugated compounds by combining photosensitizer pheophorbide-α and the anticancer drug, doxorubicin or paclitaxel. Then, we have elucidated that these conjugations inhibit the survival of various cancer cells and exhibit fluorescence when they are introduced into cells and degraded. Especially, it has been identified that the conjugate of pheophorbide-α and doxorubicin shows higher fluorescence intensity at lower pH (cancer environment).

The conjugated compounds of the present invention as therapeutics inhibiting the survival of cancer cells are synthesized in such a manner that pheophorbide-α as photosensitizers is conjugated with doxorubicin or paclitaxel as anticancer drugs. The present inventors have made an effort to develop novel substance as conjugates of pheophorbide-α and the anticancer drug, having applicability to photodynamic therapy (PDT) and cancer detection and having significantly effective anticancer efficacies. To this aim, the conjugates of the present invention have been molecularly designed and synthesized.

Because pheophorbide-α usually has photosensitivity, it has been used for photodynamic therapy. Pheophorbide-α used in the present invention may be synthesized by a variety of chemical methods known to one of skill in the art, preferably by chemically modifying chlorophyll a obtained from *chlorella*.

The term used herein "pharmaceutically acceptable salts" means those salts of the pheophorbide-α conjugates which retain pharmacological activities of interest, i.e., activities to prevent or treat cancers. These salts may be formed using inorganic acids such as hydrochloride, hydrobromide and hydroiodide, or organic acids such as acetate, adipate, alginate, aspartate, benzoate, benzenesulfonate, p-toluenesulfonate, bisulfate, sulfamate, sulfate, naphthylate, butyrate, citrate, camphorate, camphosulfate, cyclopentanepropionate, digluconate, dodecylsulfate, ethanesulfate, fumarate, glucoheptanoate, glycerophosphate, hemisulfate, heptanoate, hexanoate, 2-hydroxyethanesulfate, lactate, maleate, methanesulfonate, 2-naphthalenesulfonate, nicotinate, oxalate, tosylate and undecanoate.

The term "pharmaceutically acceptable hydrates" refers to hydrates of the pheophorbide-α conjugates which retain pharmacological activities of interest. The term "pharmaceutically acceptable solvates" refers to solvates of the pheophorbide-α conjugates which retain pharmacological activities of interest. The hydrates and solvates may be prepared using acids described herein above.

The conjugates of the present invention may comprise various anticancer drugs. The anticancer drugs used in the conjugated compounds of the present invention, which is commonly used in anticancer drugs, but is not limited to, include doxorubicin, paclitaxel, acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *bacillus* calmette-guerin (BCG), Baker's Antifol (soluble), beta-2-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxalinesulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alpha, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, navelbine, nabilone, nafoxidine, neocarzinostatin, octreotide acetate, ormaplatin, oxaliplatin, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, taxorere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, TNF (tumor necrosis factor), uracil mustard, vinblastine sulfate, vincristine sulfate, vindesine, vinorelbine, vinzolidine, Yoshi 864, zorubicin, and mixtures thereof. Preferably, the anticancer drug is doxorubicin or paclitaxel.

According to a preferred embodiment, the pheophorbide-α conjugate further comprises a chemical linker linking the first compound and the second compound.

The term "chemical linker" as used herein means an organic molecule as linkers linking pheophorbide-α and the anticancer drug. The linking of pheophorbide-α with the anticancer drug may be performed directly or indirectly via the chemical linker. The chemical linker for linking pheophorbide-α with the anticancer drug comprises a coupling moiety for coupling pheophorbide-α with the anticancer drug. Although the utilization of a chemical linker is described as an example of the present invention, the chemical linker includes not only chemically-synthesized organic molecule-containing linkers but also various amino acid linkers. Preferably, the chemical linker comprises a hydroxycinnamoyl moiety or an aminobenzyloxycarbonyl moiety.

According to a preferred embodiment, the pheophorbide-α conjugate is selected from the group consisting of compounds represented by the following Formulae 4 to 7:

(4)

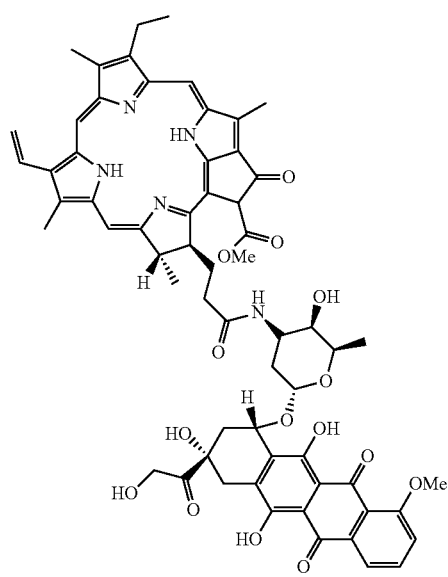

(5)

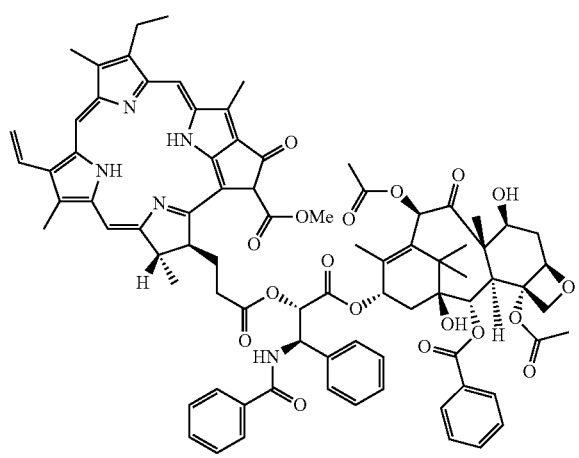

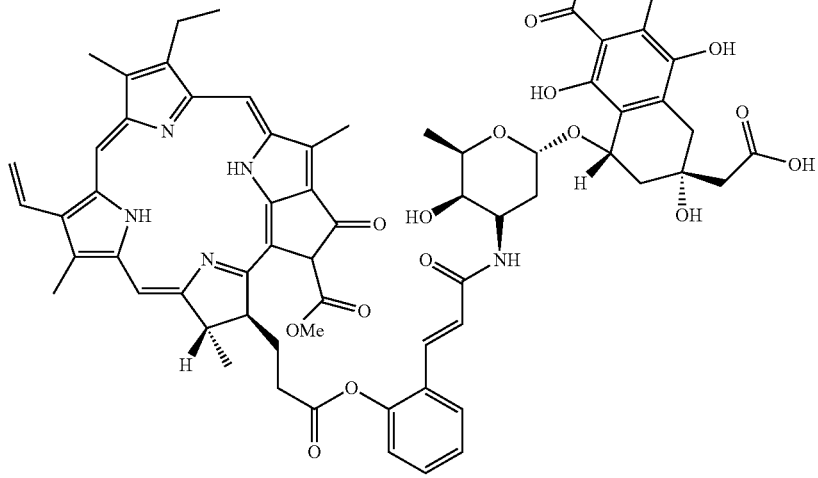

(6)

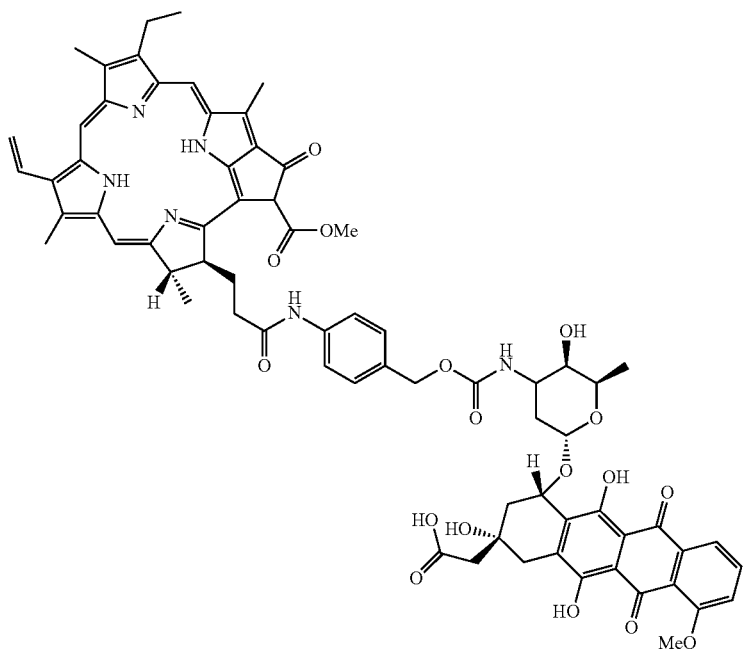

(7)

The pheophorbide-α conjugate of the present invention is significantly effective for preventing or treating cancers by inhibiting the viability of cancer cells. A pharmaceutical composition comprising the pheophorbide-α conjugate of the present invention may prevent or treat the cancers, includes breast cancer, cervical cancer, lung cancer, glioblastoma, oral cancer, pituitary adenoma, glial tumor, brain tumor, nasopharyngeal tumor, laryngeal cancer, thymoma, mesothelioma, gastric cancer, esophageal cancer, colorectal cancer, rectal cancer, liver cancer, pancreatic cancer, pancreatic neuroendocrine tumor, gallbladder cancer, penis cancer, ureter cancer, renal cell carcinoma, prostate cancer, bladder cancer, non-hodgkin lymphoma, myelodysplastic syndrome, multiple myeloma, plasma cell tumor, leukemia, pediatric cancer, skin cancer, bronchogenic carcinoma, colon cancer and ovarian cancer.

Where the composition of the present invention is used for preventing or treating cancers, it may be utilized alone or in combination with typical chemotherapy or radiotherapy. Such combination therapy may be more effective in treating cancers. The chemotherapeutic agents useful for the combination therapy include cisplatin, carboplatin, procarbazine, mechlorethamine, cyclophosphamide, ifosfamide, melphalan, chlorambucil, bisulfan, nikosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Examples of the radiotherapy useful for the combination therapy include X-ray illumination and γ-ray illumination.

The term "pharmaceutically effective amount" as used herein means an amount suitable to exhibit pharmacological efficacies as anticancer drug by killing cancer cells through photodynamic mechanism.

Where the composition of the present invention is prepared as a pharmaceutically composition, the pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. The suitable pharmaceutically acceptable carriers and agents are disclosed in detail in *Remington's Pharmaceutical Sciences* (19$^{th}$ ed., 1995).

The pharmaceutical composition according to the present invention may be orally or parenterally administered. The parenteral administration includes intravenous, intraperitoneal, intramuscular, subcutaneous and local administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. The daily dosage of the pharmaceutical composition of the present invention may be 0.0001-10000 mg/kg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

Where the composition of the present invention is provided as a photosensitizer composition for treating and detecting various cancers described above may comprise additional components generally used for photosensitizers. The photosensitizer composition of the present invention is accumulated in intracellular compartments such as endosome, lysosome, endoplasmic reticulum and golgi apparatus.

According to a preferred embodiment, the composition of the present invention shows increased fluorescence intensity at pH 3.5-4.5 compared with fluorescence intensity at pH 10.

Pheophorbide-α contained in the photosensitizer composition may be linked to, bound to or conjugated with anticancer drugs or chemical linkers described above. The light illumination for activating photosensitizers may be carried out by technologies and procedures known to one of skill in the art. For example, the wavelength and the intensity of light may be selected depending on the type of photosensitizers. Suitable light sources are well known in the art. In the methods of the present invention, the light exposure time of cells may be varied. The intracellular influx efficiency of the photosensitizer composition may be increased as increasing light exposure amount or time. The preferred time of the illumination step depends on the type of photosensitizers, the amounts of photosensitizers accumulated in target cells or tissues and the overlap between an absorption spectrum and an emission spectrum of photosensitizers. Generally, the illumination time is from a few minutes to a few hours, preferably less than 60 minutes, for example, 0.5-30 minutes, 0.5-3 minutes, 1-5 minutes, 1-10 minutes, 3-7 minutes, more preferably about 3 minutes, for example from 2.5 minutes to 3.5 minutes.

A suitable light dose may be selected by one skilled in the art, and depended on a type of photosensitizers and amounts of photosensitizers accumulated in target cells or tissues.

For example, the typically useful light dose for treating cancers by photofrin as photosensitizers and 5-aminolevulinic acid as a protoporphyrin precursor is in the range of 50-150 J/cm$^2$ under the fluence range of less than 200 mW/cm$^2$ in order to avoid hyperthermia. The light dosage generally becomes lower when photosensitizers having higher extinction coefficient at the red region of visible spectrum are used. The total light dosage required for treating non malignant tumor with less amount of accumulated photosensitizer may be substantially greater than those for treating cancers.

The features and advantages of this invention will be summarized as follows:

(a) The pheophorbide-α conjugate of the present invention exhibiting fluorescence upon its introduction into cells and degradation inhibits the survival of various cancer cells.

(b) Especially, the conjugate of pheophorbide-α and doxorubicin shows higher fluorescence intensity at lower pH (cancer environment).

(c) Therefore, the present composition for photodynamic therapy (PDT) of cancers is also very useful in detecting cancers.

(d) Interestingly, the anticancer effects of the present composition are dually exerted with help of both the photosensitizer and the anticancer drug of the present conjugates.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Methods

1. Reagents and Devices

Starting materials, reagents, and solvents were purchased from Aldrich Chemical Co. (Milwaukee, Wis.) and TCI (Tokyo) and used as supplied without further purification. Proton nuclear magnetic resonance spectroscopy was performed on a JEOL JNM-LA 300WB and 400WB spectrometer, and spectra were taken in CDCl$_3$ or DMSO-d6. Unless otherwise noted, chemical shifts are expressed as ppm downfield from tetramethylsilane as the internal standard, and J values are given in Hz. Data are reported as follows: chemical shift, multiplicity (s, singlet; d, doublet; t, triplet; m, multiplet; b, broad; app., apparent), coupling constants, and integration. Mass spectroscopy was carried out on FAB (fast atom bombardment) instruments. [FAB source: JEOL FAB source and ion gun (Cs ion beam, 30 kV acceleration)]. High-resolution mass spectra (m/z) were recorded on a FAB (JEOL: mass range 2600 amu, 10 kV acceleration) at Korea Basic Science Institute (Daegu).

1.1. Procedure for the Synthesis of Pheophorbide-α
(1)

50% ethanol in water (9 L) was treated to *chlorella* 6 L for removing polar materials and the residue was extracted twice with 100% ethanol (9 L) to obtain chlorophyll-α (4, 4.5 g). Chlorophyll-α (4, 4.0 g, 4.38 mmol) was dissolved in acetone (40 mL) and diluted with MeOH (100 mL). 1 N HCl (aq) (25 mL) was added to adjust pH 2.5 and reaction mixture was stirred for 4 h at room temperature. After 4 h, water was added in reaction flask and the mixture was stored in refrigerator for 1 day. The reaction mixture was filtered and the precipitate was obtained as a black solid, pheophytin (5, 3.38 g). Yield=88%. Pheophytin (5, 3.3 g, 3.78 mmol) was dissolved in 80% aqueous TFA (70 mL) at 0° C., which had been bubbled with nitrogen for 10 min. The resulting solution was protected from light and stirred under a nitrogen blanket at 0° C. for 1 h. The reaction mixture was concentrated to remove TFA, added to 4 N HCl (aq) (400 mL) and extracted with ethyl acetate (3×400 mL) three times. The combined organic layers were dried with $Na_2SO_4$ and concentrated. The residue was purified by silica column chromatography (chloroform:methanol=30:1) to give Pa as a black solid (1, 1.3 g). Yield=58%; 1H NMR (400 MHz, $CDCl_3$) d (ppm) 9.51 (s, 1H), 9.40 (s, 1H), 8.62 (s, 1H), 8.00 (dd, J=11.6, 6.4 Hz, 1H), 6.34-6.16 (m, 3H), 4.48 (m, 1H), 4.42 (m, 1H), 3.83 (s, 3H), 3.69 (m, 2H), 3.61 (s, 3H), 3.38 (s, 3H), 3.21 (s, 3H), 2.66-2.52 (m, 2H), 2.32-2.21 (m, 2H), 1.81 (d, J=6.8 Hz, 3H), 1.67 (t, J=7.6 Hz, 3H); ESI [M+H]=593.5; HRMS (FAB) ($C_{35}H_{36}N_4O_5$): calcd 593.2764. found 592.2690.

1.2. Procedure for the Synthesis of Pheophorbide-α-Doxorubicin (6)

EDC (50.0 mg, 0.25 mmol), HOBt (23.0 mg, 0.17 mmol), and TEA (25.0 IL, 0.17 mmol) were add to Pa (1, 50.0 mg, 0.08 mmol) in DCM (3 mL). Then, doxorubicin hydrochloride (2, 60.0 mg, 0.10 mmol) in DMF was added to the resulting solution and the reaction mixture was stirred for 4 h at room temperature. The reaction mixture was added to $NaHCO_3$ (aq) (30 mL) and extracted with chloroform (2×30 mL). The combined organic layers weredried over $MgSO_4$, concentrated and purified by silica gel column chromatography (chloroform:methanol=50:1) to give 6 as a brown sticky solid (50.0 mg). Yield: 53%; 1H NMR (400 MHz, $CDCl_3$) d (ppm) 9.22 (s, 1H), 9.17 (s, 1H), 8.43 (s, 1H), 7.91 (m, 1H), 7.54 (m, 1H), 7.39 (m, 1H), 6.94 (d, J=8.0 Hz, 1H), 6.14 (m, 3H), 5.90 (s, 1H, —OH), 4.90 (s, 2H), 4.62 (s, 2H), 4.41 (m, 1H), 4.21 (m, 2H), 4.12 (m, 1H), 4.04 (m, 1H), 3.85 (m, 3H), 3.72 (s, 3H), 3.52 (m, 2H), 3.38 (s, 1H, —OH), 3.23 (s, 6H), 3.14 (s, 3H), 3.02 (m, 1H), 2.86 (d, J=18.0 Hz, 1H), 2.60 (m, 2H), 2.36 (m, 2H), 2.04 (m, 2H), 2.01 (m, 1H), 1.85 (d, J=14.0 Hz, 1H), 1.69 (d, J=7.2 Hz, 3H), 1.62 (t, J=7.6 Hz, 3H), 1.09 (d, J=6.0 Hz, 3H); ESI [M+H]=1118.4; HRMS (FAB) ($C_{62}H_{63}N_5O_{15}$): calcd 1118.4399. found 1118.4403.

1.3. Procedure for the Synthesis of Pheophorbide-α-Paclitaxel (7)

EDC (10.0 mg, 0.06 mmol) and DMAP (0.2 mg, 0.004 mmol) were added to Pa (1, 10.0 mg, 0.02 mmol) in DCM (2 mL). Then, paclitaxel (3, 60.0 mg, 0.70 mmol) was added to the resulting solution and the reaction mixture was stirred for 4 h at room temperature. The reaction mixture was added to $NaHCO_3$ (aq) (20 mL) and extracted with chloroform (2×20 mL). The combined organic layers were dried over $MgSO_4$, concentrated and purified by silica gelcolumn chromatography (chloroform:methanol=70:1) to give 7 as a black sticky solid (11.5 mg). Yield: 54%; 1H NMR (400 MHz, $CDCl_3$) d (ppm) 9.49 (s, 1H), 9.36 (s, 1H), 8.52 (s, 1H), 8.13 (m, 2H), 8.00 (m, 1H), 7.77 (m, 2H), 7.53 (m, 1H), 7.41-7.27 (m, 10H), 7.21 (d, J=7.2 Hz, 1H, —NH), 6.30-6.16 (m, 3H), 6.08 (s, 1H), 6.05 (s, 1H), 5.69 (d, J=7.2 Hz, 1H), 5.62 (d, =3.6 Hz, 1H), 4.97 (d, =9.6 Hz, 1H), 4.45 (m, 1H), 4.30 (d, =8.4 Hz, 1H), 4.22 (m, 2H), 3.81 (d, =7.2 Hz, 1H), 3.75 (s, 3H), 3.69 (m, 5H), 3.61 (d, J=4.8 Hz, 1H), 3.38 (s, 3H), 3.21 (s, 3H), 2.67-2.51 (m, 5H, —OH), 2.45 (s, 3H), 2.42-2.29 (m, 3H), 2.21 (s, 3H), 2.18 (m, 1H), 1.94 (m, 5H), 1.87 (s, 1H, —OH), 1.79 (d, =6.8 Hz, 3H), 1.70-1.65 (m, 6H), 1.23 (s, 3H), 1.13 (s, 3H); ESI [M+H]=1429.4; HRMS (FAB) ($C_{82}H_{85}N_{18}O_5$): calcd 1428.5968. found 1428.5973.

1.4. Procedure for the Synthesis of Pheophorbide-α-Linker-Doxorubicin

1.4.1. Synthesis of pheophorbide-α-(hydroxycinnamoyl)-linker-doxorubicin. 1.4.1.1. Pheophorbide-α-2-hydroxycinnamic acid (9)

EDC (661.4 mg, 3.45 mmol), HOBt (349.7 mg, 2.59 mmol), and TEA (360.7 μL, 2.59 mmol) were added to 2-hydroxycinnamic acid (8, 283.2 mg, 1.73 mmol) in DCM (10 mL). Then, doxorubicin hydrochloride (2, 1.0 g, 1.73 mmol) in DMF was added to the resulting solution and the reaction mixture was stirred for 4 h at room temperature. The reaction mixture was added to $NaHCO_3$ (aq) (100 mL) and extracted with chloroform (2×100 mL). The combined organic layers were dried over $MgSO_4$, concentrated and purified by silica gel column chromatography (chloroform:methanol=60:1) to give 9 as a brown sticky solid (137.0 mg). Yield: 11%; 1H NMR (400 MHz, DMSO) d (ppm) 9.92 (s, 1H, —OH), 7.88 (m, 1H), 7.76 (d, J=8.8 Hz, 1H), 7.62 (m, 1H), 7.56 (d, J=16.0 Hz, 1H), 7.36 (d, J=8.0 Hz, 1H), 7.13 (t, J=8.0 Hz, 1H), 6.83 (d, =8.4 Hz, 1H), 6.78 (t, J=7.6 Hz, 1H), 6.71 (d, =16.0 Hz, 1H), 5.47 (s, 1H), 5.22 (s, 1H), 4.93 (s, 1H, —OH), 4.84 (m, 2H), 4.56 (d, J=5.6 Hz, 2H), 4.18 (m, 1H), 3.94 (s, 3H), 3.41 (s, 1H, —OH), 3.00 (m, 1H), 2.94 (m, 1H), 2.20 (m, 2H), 1.89 (m, 1H), 1.46 (m, 1H), 1.11 (d, J=6.4 Hz, 3H); ESI [M−H] =687.8.

1.4.1.2. Pheophorbide-α-2-hydroxycinnamic acid-doxorubicin (10)

EDC (64.4 mg, 0.336 mmol) and DMAP (2.5 mg, 0.02 mmol) were added to Pa (1, 100.0 mg, 0.17 mmol) in DCM (5 mL). Then, the solution of 9 (115.9 mg, 0.86 mmol) in DMF (2 mL) was added to the resulting solution and the reaction mixture was stirred for overnight at room temperature. The reaction mixture was added to NH4Cl (aq) (30 mL) and extracted with chloroform (2×30 mL). The combined organic layers were dried over $MgSO_4$, concentrated and purified by silica gel column chromatography (chloroform:methanol=70:1) to give 10 as a brown sticky solid (51.5 mg). Yield: 24%; 1H NMR (400 MHz, $CDCl_3$) d (ppm) 9.42 (s, 1H), 8.91 (s, 1H), 8.38 (s, 1H), 7.99 (d, J=15.2 Hz, 1H), 7.69 (d, J=16.8 Hz, 1H), 7.64 (d, J=6.7 Hz, 1H), 7.51 (m, 1H), 7.38 (m, 3H), 7.20 (t, J=7.6 Hz, 1H), 7.06 (d, J=8.0 Hz, 1H), 6.52 (d, J=15.6 Hz, 1H), 6.23 (s, 1H), 6.05 (d, J=8.0 Hz, 1H), 5.78 (m, 2H), 4.82 (s, 1H), 4.67 (m, 1H), 4.54 (m, 1H), 4.46 (m, 1H), 4.33 (m, 2H), 3.97-3.83 (m, 6H), 3.71-3.59 (m, 6H, —OH(1)), 3.35 (s, 1H), 3.14 (s, 3H), 3.02 (s, 1H), 2.88 (m, 2H), 2.82 (m, 2H), 2.16 (m, 2H), 1.85-1.75 (m, 6H), 1.63 (s, 4H), 1.27 (d, J=6.4 Hz, 3H); ESI [M+H]=1264.9; HRMS (FAB) ($C_{71}H_{69}N_5O_{17}$): calcd 1264.4767. found 1264.4763.

1.4.2. Synthesis of pheophorbide-α-(aminobenzyloxycarbonyl) linker-doxorubicin.

1.4.2.1. Pheophorbide-α-4-aminobenzyl alcohol (11)

EDC (485.4 mg, 2.53 mmol), HOBt (228.1 mg, 1.69 mmol), and TEA (235.3 μL, 2.59 mmol) were added to Pa (1, 500.0 mg, 0.84 mmol) in DCM (7 mL). Then, 4-aminobenzyl alcohol (104.3 mg, 0.84 mmol) in DMF was added to the resulting solution and the reaction mixture was stirred for 4 h at room temperature. The reaction mixture was added to $NaHCO_3$ (aq) (100 mL) and extracted with chloroform (2×100 mL). The combined organic layers were dried over $MgSO_4$, concentrated and purified by silica gel column chromatography (chloroform:methanol=80:1) to give 11 as a brown sticky solid (226.5 mg). Yield: 38%; 1H NMR (400 MHz, $CDCl_3$) d (ppm) 9.34 (s, 1H), 9.01 (s, 1H), 8.51 (s, 1H), 7.98 (m, 1H), 7.15 (d, J=8.4 Hz, 2H), 6.66 (d, J=8.8 Hz, 2H), 6.29 (m, 3H), 4.52 (s, 2H), 4.42 (s, 1H), 3.79 (s, 3H), 3.35 (m, 2H), 3.31 (s, 3H), 3.22 (s, 3H), 3.07 (s, 3H), 2.68 (m, 2H), 2.25 (m, 2H), 1.78 (d, J=7.2 Hz, 3H), 1.59 (t, J=7.6 Hz, 3H); ESI [M−H]=695.6.

1.4.2.2. Pheophorbide-α-4-aminobenzyl alcohol-4-nitrophenyl formate (12)

DIPEA (111.5 μL, 0.64 mmol) were added to 11 (226.5 mg, 0.32 mmol) in THF (5 mL). Then, 4-nitrophenyl chloroformate (96.7 mg, 0.45 mmol) in THF was dropwised to the resulting solution and the reaction mixture was stirred for overnight at room temperature. The reaction mixture was added to $NaHCO_3$ (aq) (70 mL) and extracted with chloroform (2×70 mL). The combined organic layers were dried over $MgSO_4$, concentrated and purified by silica gel column chromatography (chloroform:methanol=130:1) to give 12 as a brown sticky solid (85.5 mg). Yield: 41%; 1H NMR (400 MHz, $CDCl_3$) d (ppm) 9.43 (s, 1H), 9.42 (s, 1H), 8.54 (s, 1H), 8.26 (d, J=9.2 Hz, 2H), 8.04 (m, 1H), 7.36 (d, =9.2 Hz, 2H), 6.88 (d, J=8.8 Hz, 2H), 6.33-6.18 (m, 3H), 5.04 (s, 2H), 4.53 (m, 1H), 4.30 (m, 1H), 3.84 (s, 3H), 3.70 (m, 2H), 3.55 (s, 3H), 3.35 (s, 3H), 3.25 (s, 3H), 2.73 (m, 2H), 2.03 (m, 2H), 1.81 (d, J=7.2 Hz, 3H), 1.70 (t, J=8.0 Hz, 3H); ESI [M+1-1]=862.8.

1.4.2.3. Pheophorbide-α-4-aminobenzyl alcohol-4-nitrophenyl formate-doxorubicin (13)

TEA (25.8 μL, 0.19 mmol) were added to 12 (80.0 mg, 0.09 mmol) in DMF (4 mL). Then, doxorubicin hydrochloride (2, 53.7 mg, 0.09 mmol) in DMF (1 mL) was dropwised to the resulting solution and the reaction mixture was stirred for 6 h at room temperature. The reaction mixture was added to $NaHCO_3$ (aq) (40 mL) and extracted with chloroform (2×40 mL). The combined organic layers were dried over $MgSO_4$, concentrated and purified by silica gel column chromatography (chloroform:methanol=80:1) to give 13 as a brown sticky solid (21.4 mg). Yield: 19%; 1H NMR (400 MHz, $CDCl_3$) d (ppm) 9.19 (s, 1H), 9.14 (s, 1H), 8.39 (s, 1H), 7.90 (m, 1H), 7.42 (d, =7.2 Hz, 1H), 7.17 (t, J=8.0 Hz, 1H), 6.87 (m, 4H), 6.64 (d, J=6.8 Hz, 1H), 6.25 (m, 3H), 6.15 (d, J=6.8 Hz, 1H), 4.90 (s, 1H), 4.72 (m, 4H), 4.43 (m, 1H), 4.18 (m, 3H), 3.90 (m, 1H), 3.79 (s, 3H), 3.70 (m, 2H), 3.59 (m, 5H), 3.47 (s, 1H), 3.30 (s, 1H), 3.21 (s, 3H), 3.19 (s, 3H), 3.05 (m, 1H), 2.98 (m, 1H), 2.67 (m, 2H), 2.24 (m, 2H), 2.06 (m, 2H), 1.77 (m, 1H), 1.72 (m, 4H), 1.60 (s, 3H), 1.18 (d, J=6.0 Hz, 3H); ESI [M+H]=1268.1; HRMS (FAB) ($C_{70}H_{71}N_6O_{17}$): calcd 1267.4876. found 1267.4871.

2. HPLC Analysis

HPLC was used for purification of all final products. The purification was performed on a Shimadzu SCL-10A VP HPLC system using a Shimadzu Shim-pack C18 analytical column (250 mm×4.6 mm, 5 μM, 100 Å) in isocratic solvent systems. Solvent system was 0.1% TFA in H2O:CH3CN=5:95 over 30 min at a flow rate=1 mL/min. Peaks were detected by UV absorption using a diode array detector.

3. Cell Viability Assay

3.1. Cell Culture

The AT-84 is a squamous cell carcinoma, spontaneously arising from oral mucosa and syngenic to C3H/HeJ mice (which were kindly provided by Dr. E. J. Shillitoe, State University of New York, Upstate Medical University). MCF7, KB, HCT116, PC3, U-87MG, SK-OV-3, AT-84 cells were grown in RPMI 1640. The adherent cell line HepG2, HeLa, A549, YD-10B cells were cultured in DMEM medium. Both media were supplemented with 10% FBS (Invitrogen Co.), and antibiotic-antimycotic (Invitrogen Co.). All cell lines were incubated in a humidified atmosphere containing 5% CO2 at 37° C. The adherent cells were detached from the culture flasks by removal of the growth medium and addition of 1 mL trypsin/EDTA solution (0.05% w/v trypsin, 0.016% w/v EDTA). After 1-2 min incubation at 37° C., when the cells had detached from the surface, trypsinization was stopped by the addition of 4 mL of DMEM medium containing 10% FBS.

3.2. SRB (Sulforhodamine B) Assay

The cells were plated at a density of 50,000 cells/mL and well in 96-well plates and incubated with inhibitors for the time indicated. The SRB assay was carried out as described by Skehan et al. (Skehan, P. et al., J. Natl. Cancer Inst. 1990, 82, 1107). The drug incubation period of the cells was stopped by the addition of 50 μL of ice cold TCA solution into the growth medium.

4. Fluorescence Spectrometry

Fluorescence measurements were done using a FluoroMate FS-2. Steady-state fluorescence spectra were generally taken at 1 μM of compounds (1, 2, 6, 10, and 13) and 0.5 μM of compound 7 in MeOH. The samples were illuminated with 420 and 440 nm of light and fluorescence emission was scanned from 500 to 800 nm. Fluorescence spectra in both aqueous and organic solvent were generally taken at 1 μM of compound 6 and 0.5 μM of compound 7 in 100% MeOH and 50% aqueous MeOH by illumination with 420 nm of light. The pH profiles of fluorescence spectra were generally taken at 1 μM of compound 6 and 0.3 μM of compound 7 at pH 4 and 10 in MeOH by illumination with 420 nm of light.

5. Confocal Fluorescence Microscopy

HeLa Cells were plated in the slide dishes and incubated in RPMI 1640 medium for overnight. The next day, compound of 10 μM in complete medium was added and incubated for 48 h in a humidified atmosphere of air/CO2 (95%:5%). After washing three times with PBS, the cells were viewed under a FluoView™ FV1000 ConfocalMicroscope. Compounds' fluorescence was observed at 440 nm for an excitation wavelength and at 575-600 nm and 655-755 nm for an emission wavelength. The images of Pa (1) and DOX (2) were assigned as red and green color.

Results and Discussion

1. Synthesis of Chemicals

Scheme 1

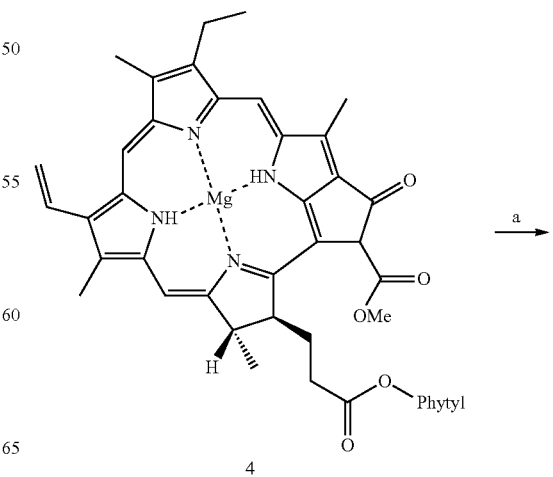

15
-continued

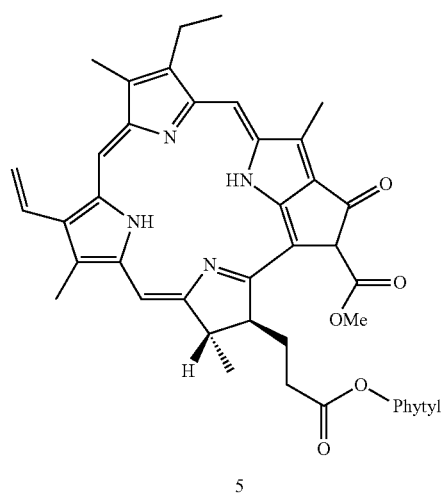

5

16
-continued

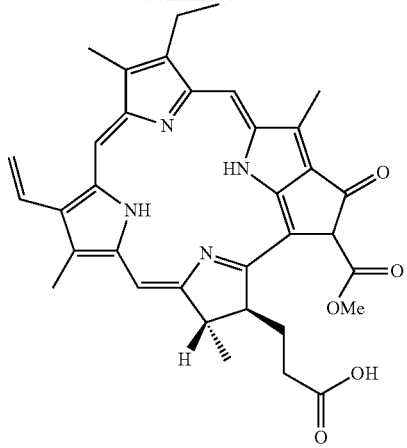

1

The general synthetic procedure for pheophorbide-α (Pa, 1) is described in Scheme 1. Treatment of the ethanol solution of chlorophyll a (4) (Jong-Hwan, P. et al., Plant Cell Physiol. 2009, 50, 719) in an acidic condition (1 N HCl, pH 2.5) enabled to remove the $Mg^{2+}$ ion easily to afford a crude pheophytin (5) in the form of precipitate. The pheophytin (5) was subsequently hydrolyzed by reacting with 80% TFA in water to afford pheophorbide-α as a fine powder. The synthesized Pa was conjugated directly or indirectly using self-immolative linkers with doxorubicin (DOX, 2) or paclitaxel (PTX, 3).

Scheme 2

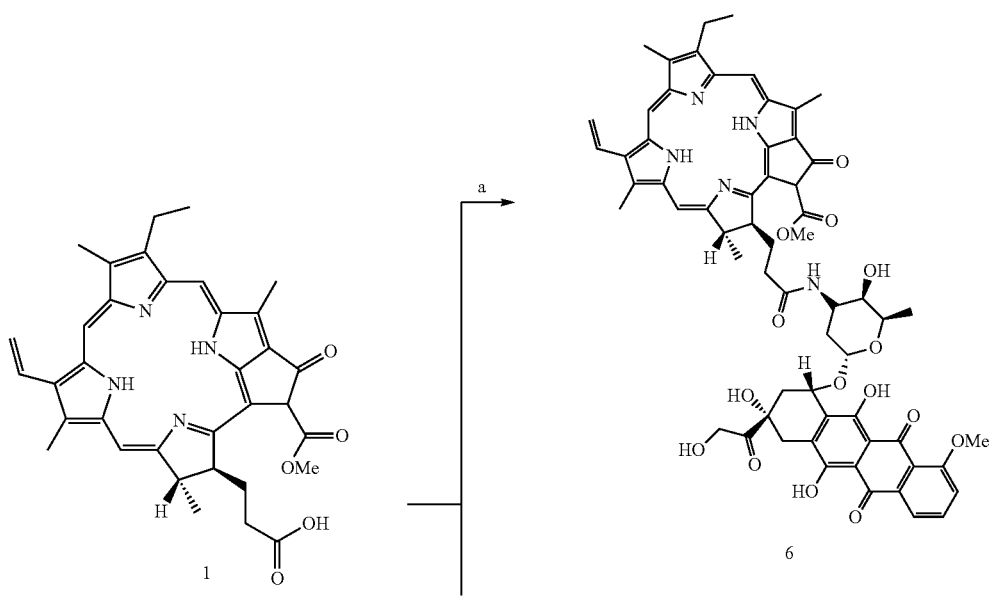

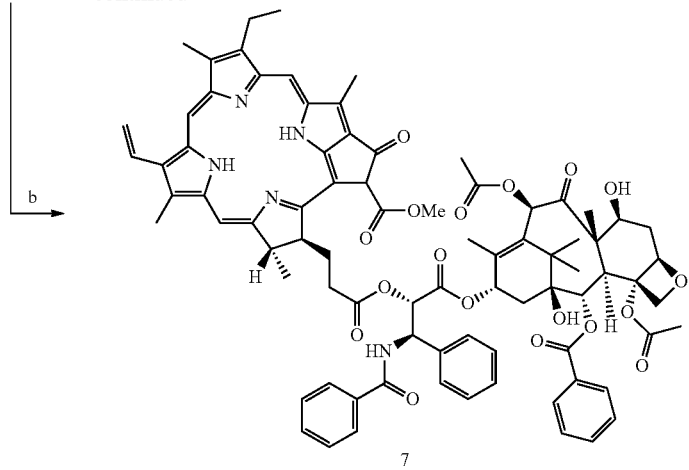
20
The directly conjugated product, Pa-DOX (6) and Pa-PTX (7) were synthesized by the reaction using EDCI as a coupling reagent (Graham, B. J. et al., Bioorg. Med. Chem. Lett. 2000, 10, 1987; Pickaert, G. et al., J. Org. Chem. 2004, 69, 5335) (Scheme 2).
Scheme 3
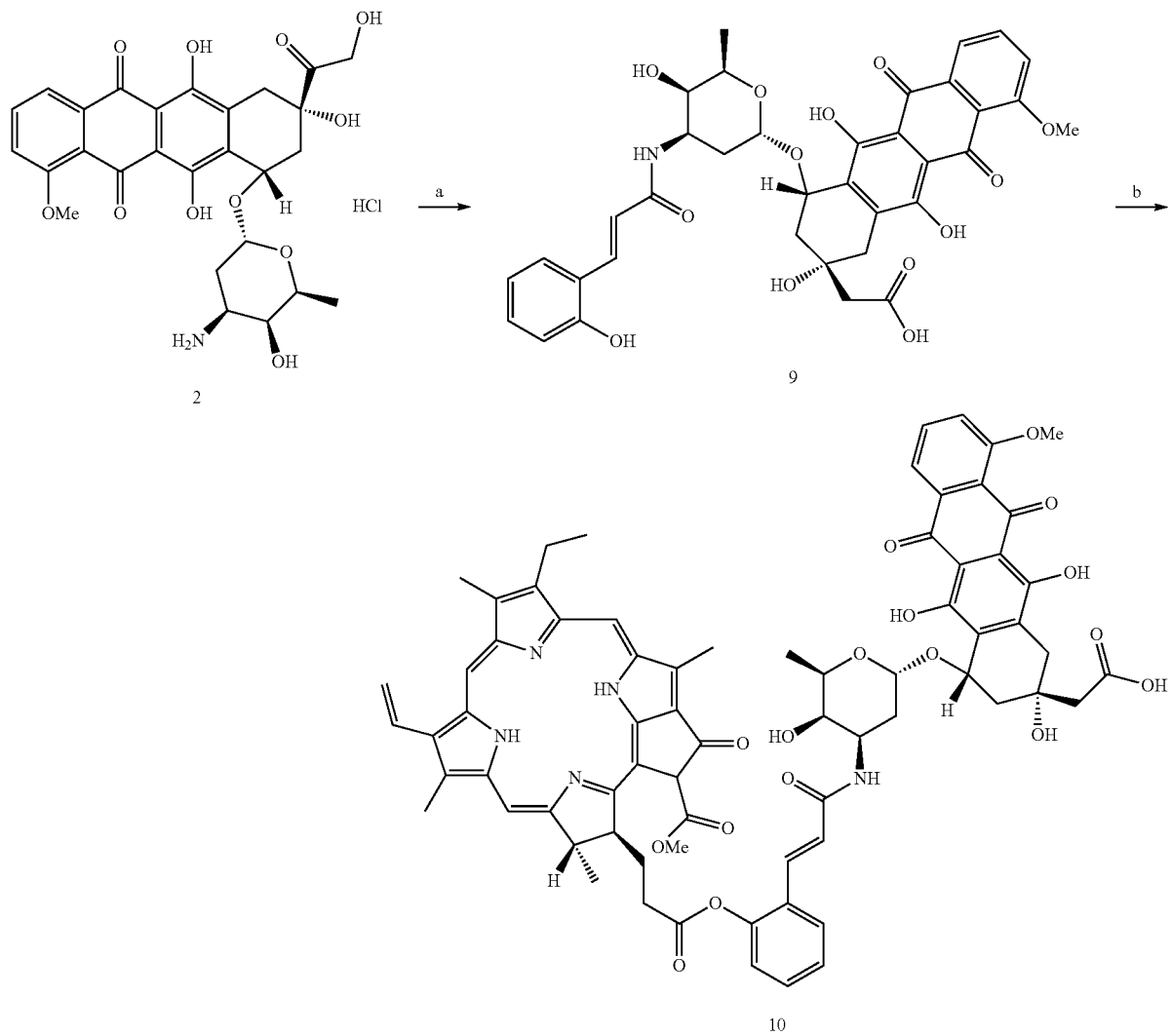

Scheme 4

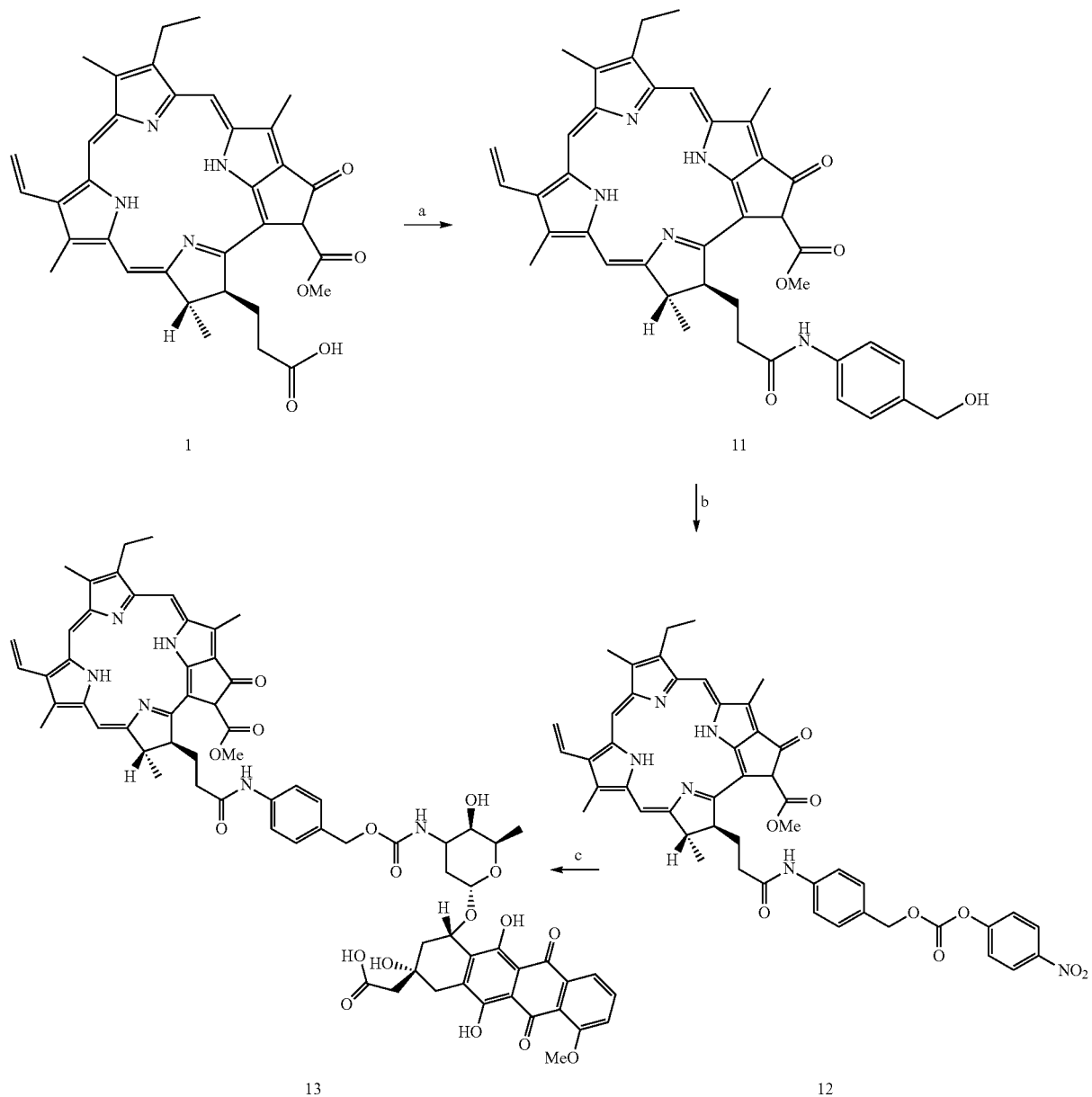

For the synthesis of Pa-DOX conjugates (10 and 13), hydroxycinnamoyl moiety and aminobenzyloxycarbonyl moiety as self immolative linkers were employed. Briefly, 2-hydroxycinnamic acid (8) was first reacted with doxorubicin hydrochloride (2) and subsequently reacted with Pa (1) using EDCI as a coupling reagent to produce the Pa-(hydroxycinnamoyl)linker-DOX compound (10) (Scheme 3). For the aminobenzyoxycarbonyl linker, Pa (1) was coupled with 4-aminobenzyl alcohol to synthesize compound (11), which was further reacted with 4-nitrophenyl chloroformate to afford carbonate ester compound (12). Finally, doxorubicin hydrochloride (2) and compound (12) were conjugated to synthesize the Pa-(aminobenzyloxycarbonyl) linker-DOX compound (13) bearing the carbamate ester (Scheme 4).

2. Cell Viability Study

A cell viability assay was conducted to test the synthesized compounds on various cancer cells including MCF7 (breast adenocarcinoma), KB (mouth carcinoma), HeLa (cervical cancer), U-87MG (glioblastoma), A549 (lung adenocarcinoma), AT-84 (oral cancer), and YD-10B (oral cancer) cells. Briefly, the cells were incubated for three days with the synthesized compounds (6, 7, 10, and 13) and the viability was measured by the protocol of SRB assay. The activity of the compounds is shown in FIG. 2. The results showed that 10 μM of Pa-DOX direct conjugate (6) moderately inhibited the growth of cancer cells including MCF7, HeLa, U-87MG, and AT-84 cells, but lower activity than DOX itself. Although the tumor specific self-immolative linkers in the conjugates (10 and 13) would be theoretically cleaved to generate Pa and DOX, the Pa-linker-DOX compounds showed generally less inhibitory activity of the cell viability compared to the same concentration of Pa-DOX direct conjugate. The results may be interpreted with possibilities that the conjugates may suffer from entering the cells or being cleaved in the cells. Infact, the cellular uptake of the conjugates was occurred slower than Pa itself as shown in the study of Section 2.4. On the other hand, Pa-PTX conjugate (7) showed potent inhibitory activity of the viability of MCF7, HeLa, KB, and YD-10B cells at 10 µM. Therefore, the ester bond between Pa and PTX in the conjugate (7) may be more easily cleaved than the amide bond of Pa-DOX conjugates in those cancer cells.

3. Analysis of Fluorescence Spectrum

Figure 3A:
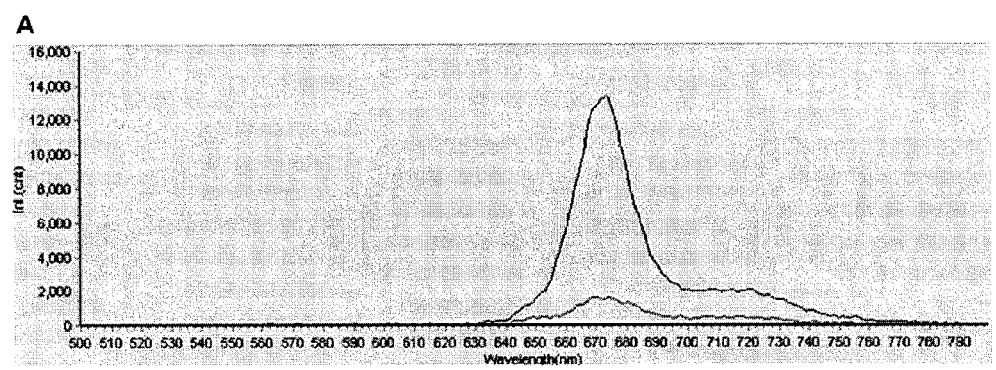
FIGS. 3a-3b represent Fluorescence spectra of compounds 6 (A) and 7 (B) in organic and aqueous solvent with 420 nm excitation wavelength. The emission wavelength in MeOH and aqueous solvent was shown in blue and red, respectively.
Figure 3B:
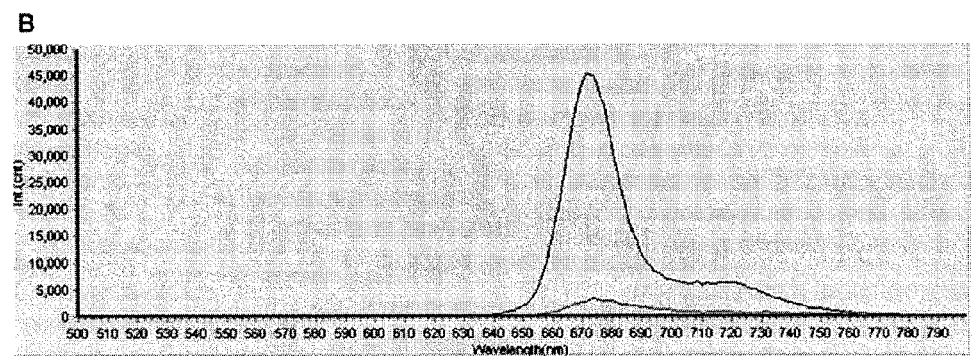
Figure 4A:
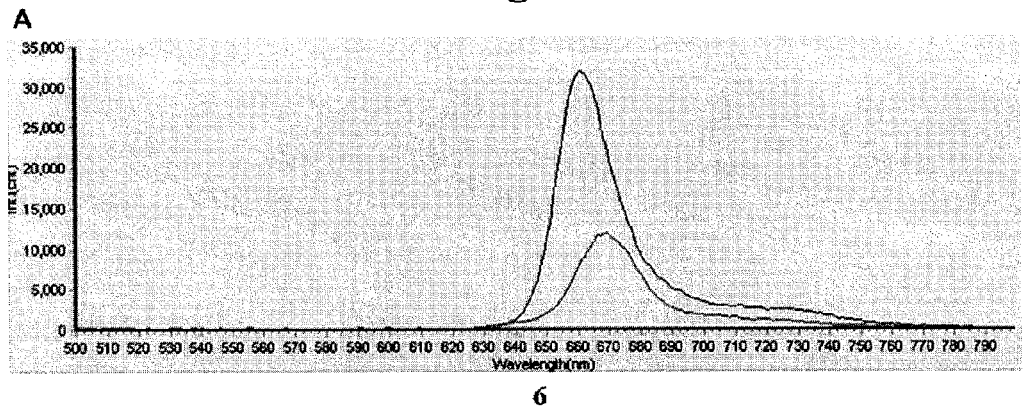
FIGS. 4a-4b represent pH profile of fluorescence spectra of 6 (A) and 7 (B) at pH 4 and 10 with 420 nm excitation wavelength. The emission wavelength at pH 4 and 10 was shown in blue and red, respectively.
Figure 4B:
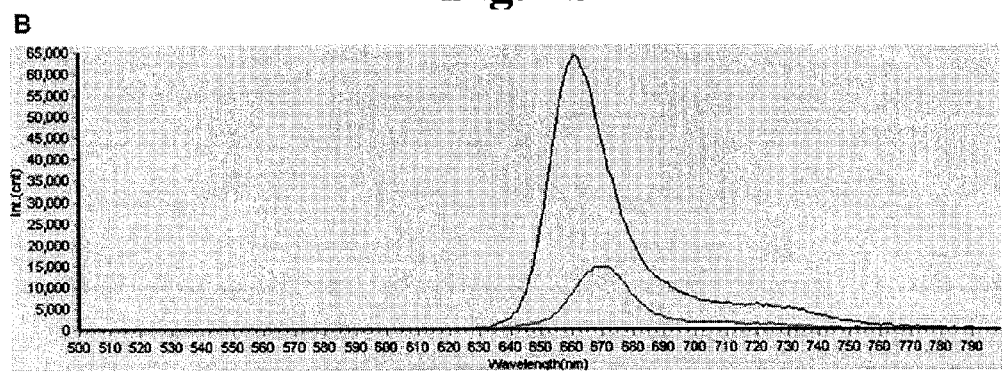
Figure 5:
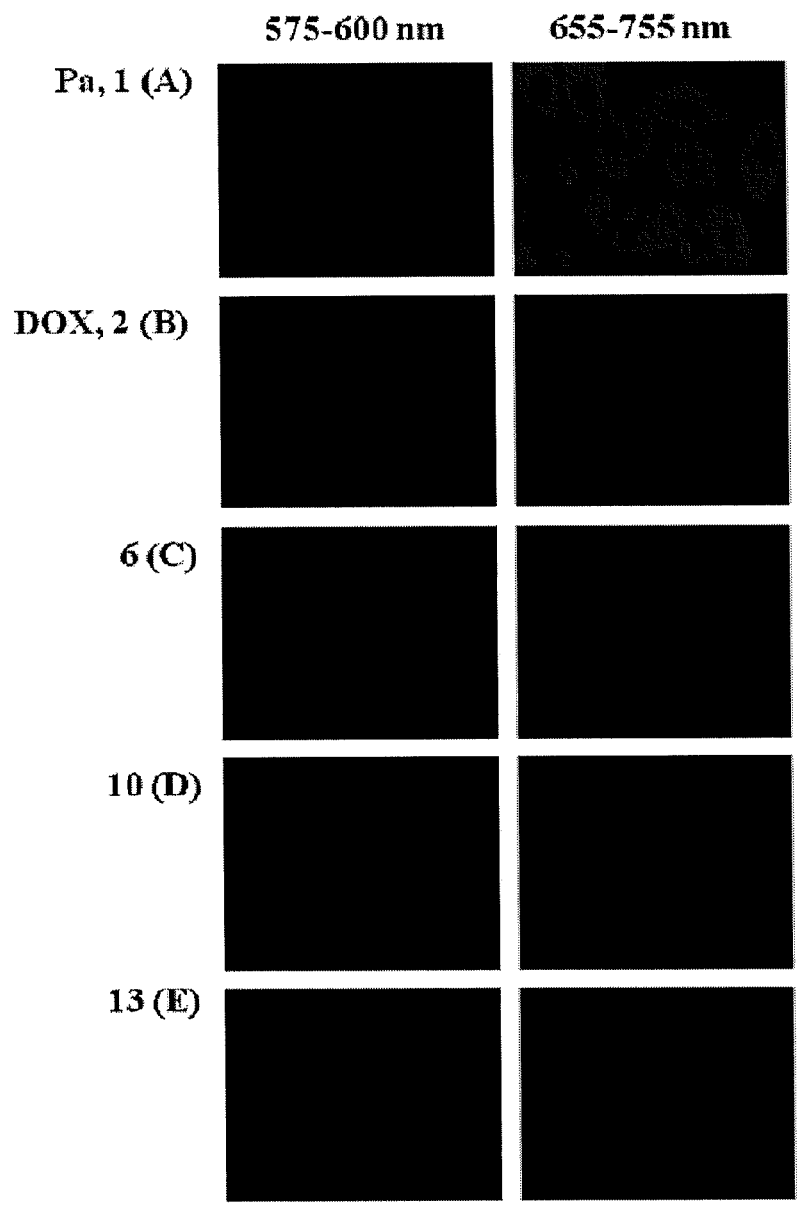
FIG. 5 represents confocal fluorescence microscope images on HeLa cell after incubation with 10 µM Pa (A), DOX (B) and conjugates (C-E) for 48 h. 575-600 nm emission wavelength with 440 nm excitation wavelength was shown in green, and the 655-755 nm emission wavelength with 440 nm excitation wavelength was shown in red.

To determine fluorescence quenching effect of the conjugates, the intensity of fluorescence of each compound with same concentration was analyzed using fluorescence spectrophotometer. The fluorescence emission spectrum of compounds at 1 µM (1, 2, 6, 10, and 13) and 0.5 µM (7) was obtained by excitation wavelengths (420 and 440 nm). The fluorescence emission of Pa (1) showed a peak at 665 nm, the highest fluorescence being generated by 420 nm excitation. The fluorescence emission of DOX (2) showed a peak at 585 nm either by 420 and 440 nm excitation. The fluorescence emission of Pa-DOX conjugate (6, 10, and 13) showed a peak at 670 nm, the highest fluorescence being generated by 420 nm excitation. The fluorescence intensity of the emission at 670 nm of all conjugates of Pa-DOX was significantly less than that of Pa when excited at 440 nm. This data suggested that photo-activity of the conjugates may be suppressed by the self-quenching effect between Pa and DOX. Therefore, it could be speculated that the background fluorescence of the conjugates as they are administered invivo, may not be detected until internalization and cleavage of the conjugates by enzymatic attack in cancer cells are occurred so that the photoactivity of Pa and DOX may be recovered. In the case of Pa-PTX conjugate (7), fluorescence quenching effect was not observed as PTX is not a fluorophore (FIG. 3). To verify fluorescence quenching due to a close contact effect, spectral comparison of fluorescence emission of compounds 6 (1 µM) and 7 (0.5 µM) in aqueous and organic solvent was investigated by 420 nm excitation wavelength using fluorescence spectrophotometer. In contact quenching, two molecules interact by proton-coupled electron transfer through the formation of hydrogen bonds. In aqueous solutions, electrostatic, steric and hydrophobic forces control the formation of hydrogen bonds. Therefore, the quenching efficiency of conjugates could depend on the employed solvents. In fact, the intensity of fluorescence of conjugates (6 and 7) in 50% aqueous MeOH was significantly reduced compared with that in 100% MeOH. This data suggested that two molecules of the conjugates stack together by proton-coupled electron transfer through the formation of hydrogen bonds to form ground state complex, nonfluorescent species as a contact quenching mechanism because energy transfer was not observed with the conjugates (FIG. 4). Since the environment of cancers generally exhibits lower pH, fluorescence profiles of conjugates, 6 and 7 either in acidic and basic conditions were explored by measuring the emission spectrum and intensity of fluorescence of compounds 6 (1 µM) and 7 (0.3 µM) at pH 4 and 10 using 420 nm of excitation wavelength. The emission spectra of fluorescence of 6 and 7 at pH 4 were blue-shifted about 10 nm from those at pH 10 and the intensity of fluorescence was increased at pH 4 but decreased at pH 10. These results suggested that higher fluorescence of the conjugates at lower pH as in the case of cancer environment may be advantageous in utilizing them for the fluorescence detection of cancers (FIG. 5).

4. Cellular Uptake Study by Confocal Fluorescence Microscopy

The cellular uptake of compounds (2, 6, 10, and 13) with different structural features was examined using confocal microscopy. For the measurement of cellular localization of the conjugates when they are cleaved, confocal microscopy was performed in HeLa cells based on the cell viability assay result. In a preliminary study, HeLa cells pretreated with compounds at 10 µM exhibited fluorescence at 570-600 nm and 655-755 nm emission when excited at 440 nm, which are corresponding to those of DOX and Pa, respectively, according to the fluorescence microscopy data. The fluorescence confocal images of HeLa cells after incubation with compounds for 48 h are shown in FIG. 6, where the fluorescence of the Pa is shown in red and the fluorescence of the DOX is shown in green, respectively. Although Pa-DOX conjugates incubated with HeLa cells emitted lower fluorescence intensity compared with free Pa and DOX, the florescence corresponding to DOX and Pa, the components of conjugates was gradually increased up to 48 h, which could be detected only when the cleavage occur. Therefore, the conjugates of Pa-DOX system developed in this study may possess the potential properties to be used in cancer diagnosis as well as therapeutic treatment such as more efficient photodynamic therapies. Since Pa-linker-DOX conjugates showed similar behavior of uptake and cleavage to that of Pa-DOX, the reported cancer specific linkers seems not to be effective in the system for the Pa-DOX conjugates.

CONCLUSION

New conjugates of photosensitizer and the anticancer drug using pheophorbide-α and doxorubicin showed potential characteristics of cancer diagnosis as well as cancer therapeutics by the study of inhibitory activities of cancer cell viability and background fluorescent quenching effect of the conjugates, and cellular uptake and cleavage monitored by confocal fluorescence microscopy. Also, dual anticancer effect by the photosensitizer, Pa in photodynamic therapy and anticancer drug, DOX after cell uptake and cleavage could be expected and further study on this field is in progress.

Having described a preferred embodiment of prevent invention, it is to be understood that variants and modifications thereof falling within the spirit of the invention may become apparent to those skilled in this art, and the scope of this invention is to ve determined by appended claims and their equivalents.

What is claimed is:
1. A pheophorbide-α conjugate comprising: (i) a first compound represented by the following Formula 1 and a second compound represented by the following Formula 2; or (ii) a first compound represented by the following Formula 1 and a second compound represented by the following Formula 3:

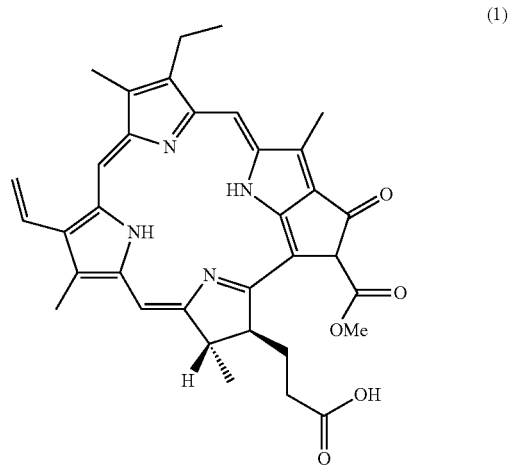

(1)

(2)

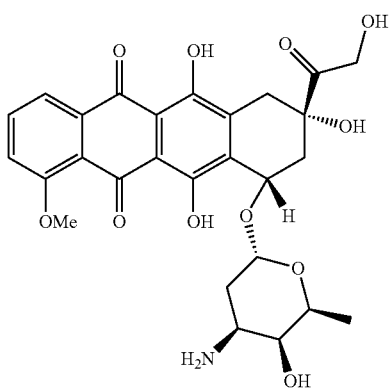

(3)

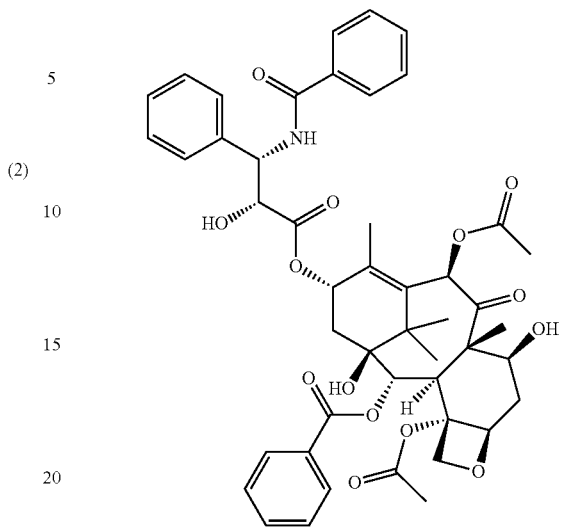

or a pharmaceutically acceptable salt, or solvate thereof.

2. The pheophorbide-α conjugate according to claim 1, wherein the pheophorbide-α conjugate further comprises a chemical linker linking the first compound and the second compound.

3. The pheophorbide-α conjugate according to claim 2, wherein the chemical linker is a hydroxycinnamoyl moiety or an aminobenzyloxycarbonyl moiety.

4. The pheophorbide-α conjugate according to claim 1, wherein the pheophorbide-α conjugate is selected from the group consisting of compounds represented by the following Formulae 4 to 7:

(4)

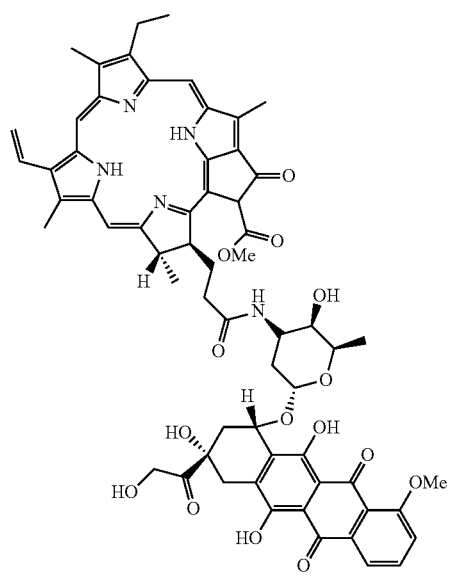

(5)

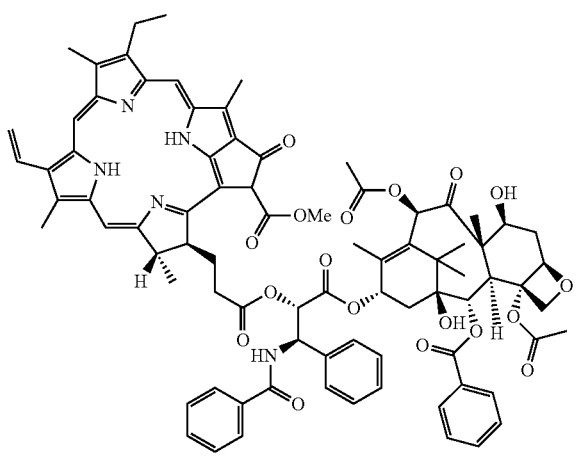

-continued
(6)
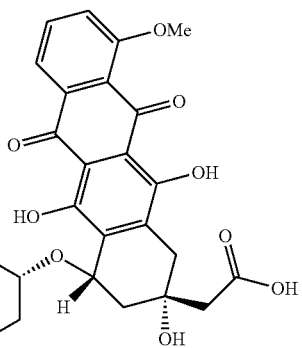
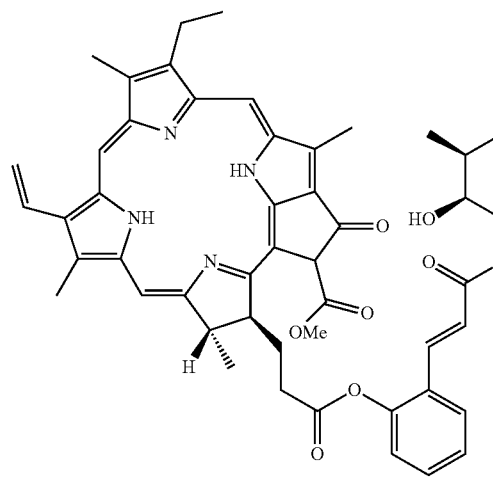
(7)
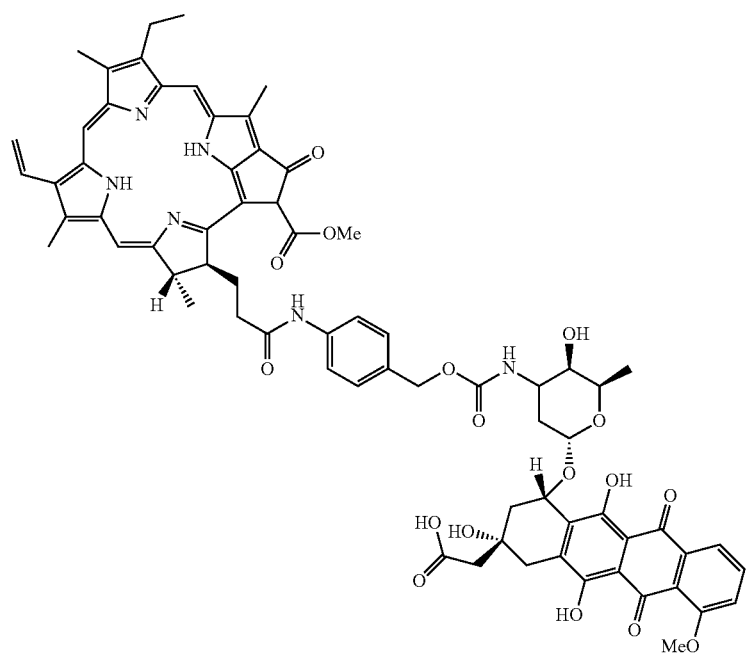
5. A pharmaceutical composition comprising: (a) a pharmaceutically effective amount of the pheophorbide-α conjugate according to claim 1; and (b) a pharmaceutically acceptable carrier.
* * * * *